United States Patent [19]

Jansson et al.

[11] Patent Number: 4,656,663
[45] Date of Patent: Apr. 7, 1987

[54] METHOD OF FILM INSPECTION WITH A MICROSCOPICAL IMAGE ANALYZER

[75] Inventors: Peter A. Jansson, Hockessin; Michael J. Merrill, New Castle, both of Del.; Daniel K. Owens, Circleville, Ohio; Barry Rubin, Glen Mills, Pa.

[73] Assignee: E. I. Du Pont de Nemours and Company, Wilmington, Del.

[21] Appl. No.: 637,801

[22] Filed: Aug. 6, 1984

[51] Int. Cl.⁴ .............................................. G06K 9/00
[52] U.S. Cl. ............................................ 382/8; 427/10
[58] Field of Search ...................... 382/8, 18, 50, 51, 6; 356/335, 336, 239; 377/6, 10, 11; 427/8, 10

[56] References Cited

U.S. PATENT DOCUMENTS

| | | | |
|---|---|---|---|
| 3,976,382 | 8/1976 | Westby | 356/376 |
| 4,525,376 | 6/1985 | Edgerton | 427/10 |
| 4,567,610 | 1/1986 | McConnell | 382/18 |

OTHER PUBLICATIONS

D. K. Owens, "The Surface Structure of Transparent Films . . . ", *Proc. Int. Microscopy Symp.*, Chicago, 1960.
P. A. Jansson et al., "Implementation and Application of a Method . . . ", *Electrophoresis*, 1983, 4, pp. 82–91.

*Primary Examiner*—Stephen A. Kreitman

[57] ABSTRACT

An automated system is used for the inspection of a transparent film which has been metallized by vaporizing a metal so that it impacts the film's surface at a preselected angle, wherein the metallized film sample is illuminated with a light source, and the transmitted light is passed through a microscope to a video camera, which produces a videoscan. The videoscan is digitized, stored in a computer memory, and processed pixel by pixel by the computer which calculates asperity height distribution from the number and lengths of metallizing shadows caused by asperities on the film surface. This method is especially useful for inspecting film to be used for recording devices, especially for video tapes, where accurate information on the asperity height distribution is required.

5 Claims, 6 Drawing Figures

MIA ASPERITY ANALYSIS

```
FILM TYPE: 75 XM 202
MILL ROLL NO.: 5310255          DATE MFD: 20 FEB 84
DATE TESTED: 23-FEB-84          TIME: 14:11:24
ANALYST: KO
REMARKS:

RESULTS

AREA SURVEYED: (mm^2)      0.111
TOTAL ASPERITY NO.         283.
TOTAL ASPERITY NO./mm^2:   2556.
MEAN ASPERITY HT: (um)     0.22
MEDIAN ASPERITY HT: (um)   0.26
STANDARD DEVIATION: (um)   0.13
```

FIG. 6

```
                 DISTRIBUTION

HEIGHT - um              NUMBER      NUMBER/mm^2

0.1                      111          1003.
  0.2                       69           624.
  0.3                       54           488.
  0.4                       31           281.
  0.5                       12           109.
  0.6                        5            46.
  0.7                        3            28.
  0.8                        1            10.

HISTOGRAM 0.1   **********************************************************
  0.2   ****************************************
  0.3   *******************************
  0.4   *****************
  0.5   ******
  0.6   ***
  0.7   **
  0.8   *
  0.9
  1.0
1.1 - 1.2
1.3 - 1.4
1.5 - 1.6
1.7 - 1.8
1.9 - 2.0
2.1 - 2.2
2.3 - 2.4
2.5 - 2.6
2.7 - 2.8
2.9 - 3.0
 >= 3.1
        :---------:---------:---------:---------:---------:---------:
        0.0                                                    120.00
2.0 ASPERITIES GIVE ONE *

SHADOW FACTOR:         3          EO MAX= 44.00
NO. OF FIELDS:        25          EO MIN= 28.00
MAGNIFICATION:    165.00          EO AVG= 34.28
SMALLEST PARTICLE:  0.10 um
THRESHOLD FACTOR:   0.40
```

METHOD OF FILM INSPECTION WITH A MICROSCOPICAL IMAGE ANALYZER

BACKGROUND OF THE INVENTION

This invention relates to a method of using an integrated, automatic analytical system for determining the distribution and the sizes of small particles present on the surface of certain polymer films, especially those used for special applications such as, for example, videotapes.

The polymer most commonly used for videotape film manufacture is poly(ethylene terephthalate). However, the technique of this invention is equally applicable to films of other materials, and the general principle on which this invention is based was originally developed for ordinary transparent packaging films, such as cellophane films, for determining their surface characteristics.

It is customary during the manufacture of poly(ethylene terephthalate) films to be used for making videotapes to add small particles to the film surface to reduce friction in windup. In order to obtain optimum surface properties, the height distribution of surface peaks (called asperities) must be carefully measured and controlled.

A paper by D. K. Owens presented at the International Microscopy symposium in Chicago in June 1960, and published in the "Proceedings" of that symposium, describes a technique for examining the surface of a transparent film known as metal shadowing. Briefly, the technique consists of metallizing the film surface by vacuum evaporation of the selected metal so that it travels from the vapor source to the film surface at an angle other than 90°. Because of this angular path, the metal will not deposit behind asperities present on the film surface, creating clear areas known as "metallic shadows". The height of each asperity can be readily calculated from the length of the metallic shadow behind it and the angle of impact or "shadowing angle".

Such examinations were done in the past by photographing a selected metallized film surface with a camera attached to a light microscope, and then manually scanning the photographic plate, measuring the lengths of metallic shadows, and calculating the height distribution of the asperities. This operation was very slow and tedious and inherently error-prone.

There is, therefore, a need for improving the efficiency and accuracy of such metallized film surface examinations.

SUMMARY OF THE INVENTION

According to the present invention, there is provided in a method of inspecting a transparent film having asperities distributed over its surface, that includes the steps of metallizing the film surface by vapor deposition of a metal impacting the film surface at a preselected shadowing angle to form transparent metallizing shadows adjacent to each asperity, illuminating a metallized film sample, and examining an area of the film surface with an optical microscope placed in the path of the light illuminating the sample and transmitted through the metallizing shadows to determine the number and lengths of said metallizing shadows and therefrom the asperity height distribution, the improvement comprising:

(a) scanning the field of view of the microscope with a video camera to detect metallizing shadows therein, (b) generating signals responsive to the transmitted light intensity for each metallizing shadow and comparing them with a calculated threshold value adapted to each image, and (c) from the signal amplitudes at least equal to the threshold values and from the preselected shadowing angle, automatically calculating the asperity height distribution within the field of view.

BRIEF DESCRIPTION OF THE DRAWINGS

FIG. 6 is a typical computer printout produced by the apparatus of this invention.

DETAILED DESCRIPTION OF THE INVENTION

As disclosed by D. K. Owens in Proceedings of the International Microscopy Symposium, Chicago, June 1960, pp. 200–203, aluminum is for many reasons the most satisfactory metal for vapor deposition on a transparent film. While the following discussion will occasionally refer to aluminum, the invention is not limited to the use of that metal. Other suitable, but less practical, metals include, for example: gold, silver, platinum, chromium, zinc, etc. A suitable metal should be readily available and thus inexpensive, resistant to oxidation, and capable of being vaporized at moderately high temperatures, e.g. 1000°–1200° C.

Figure 1:
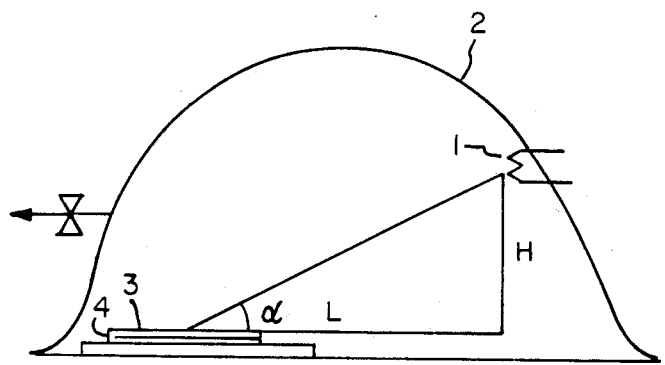
FIG. 1 is a schematic diagram of the transparent film metallization step.

Referring to FIG. 1, which schematically illustrates the metallization step, aluminum wire is placed in contact with an electrically heated element such as tungsten wire 1 in a glass vacuum bell jar 2 at a height H. A film sample 3, mounted on a standard glass microscope slide 4, is placed horizontally, the film side up, in the bell jar at a horizontal distance L from the heat source 1 to the center of the glass slide area to be metallized. The bell jar is evacuated to a sufficiently low pressure, e.g., 1.3 Pa or less, and aluminum is vaporized from the hot tungsten wire until the test film's light transmission is reduced to about 10–20%.

Because of the angle, $\alpha$, at which aluminum vapor impacts the film surface, there will remain behind each asperity a high transparency area, substantially free of aluminum deposit. This area is normally referred to as "shadow", and the angle at which aluminum impacts the test film is known as the "shadowing angle". That angle, $\alpha$, is best defined in terms of its arc tangent, which is expressed as follows:

$$\arctan \alpha = H/L$$

It has been found practical to choose a shadowing angle $\alpha$ such that $\arctan \alpha = \frac{1}{3}$.

Figure 2:
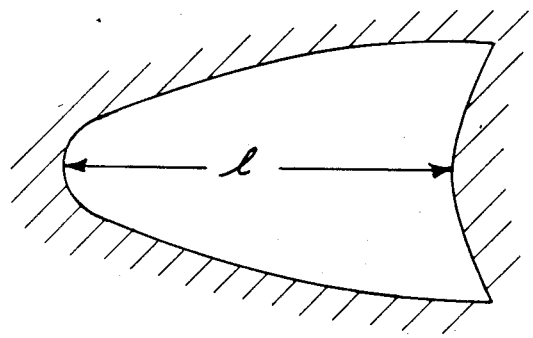
FIG. 2 is a view showing the transparent "shadow" formed behind an asperity following the metallization step.

FIG. 2 represents a view of a metallizing shadow, wherein l is the longest length of the shadow (always in the direction of shadowing). Since l corresponds to the highest point on the surface of the asperity, the height of the asperity, h can be calculated from the equation:

$$h = (H \cdot l)/L$$

and, for the particular shadowing angle chosen: $h = \frac{1}{3}l$. Since for a high power optical microscope it is possible to obtain a resolution of about 0.3 μm, the detectable asperity height is about 0.1 μm.

The purpose of the microscopic image analyzer of this invention is to measure the l values for all the detectable metallizing shadows in the field of view and to determine therefrom the heights of all the asperities within that field of view and to provide asperity height distribution information.

The metallized film surface is observed through a high quality (and usually high power) microscope, and the microscope image is scanned by a video camera. The videoscan produced by the camera is converted to digital form and stored in a computer memory, from which the stored information is retrieved by the computer and processed by the computer to provide the required information. A display means is provided as an aid in the practical execution of the microscopical image analysis.

Figure 5:
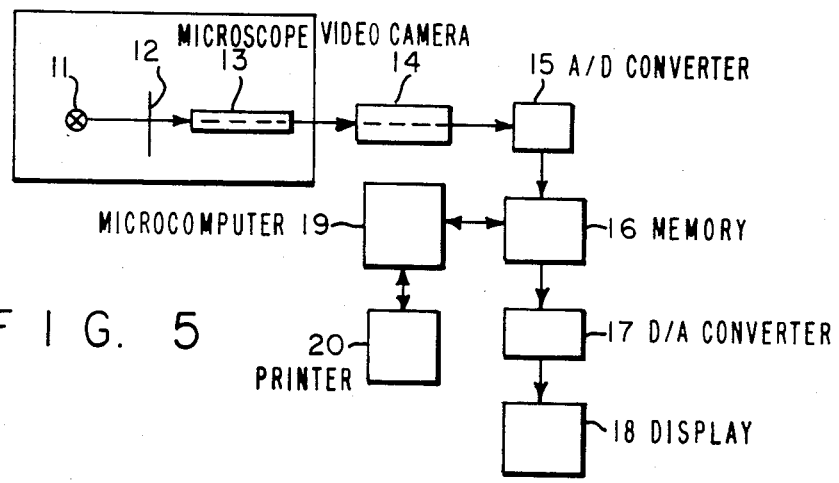
FIG. 5 is a block diagram of a film inspection system according to the present invention.

Referring to FIG. 5, which is a schematic drawing of the microscopical image analysis apparatus of the present invention, 11 is a light source (usually, part of the microscope itself), which illuminates a metallized film sample 12, through which light is transmitted to microscope 13 and then to video camera 14. Video camera 14 produces a videoscan, which is digitized by means of analog-to-digital converter 15 and sent to memory means 16. The memory means is connected, through digital-to-analog converter 17, to display means 18, which permits the operator to follow the progress of certain calculations, as well as to obtain a display of various calculation results. The memory means is also connected to microcomputer means 19 capable of performing the required calculations on information which it retrieves from memory means 16. The computer has its usual peripheral equipment, including a terminal for operator input and a printer 20 for producing a permanent record of the microscopical image analysis.

The image corresponding to the entire field of view is stored in an array of picture elements (pixels). The number of pixels depends on the image memory used, and the video camera must be able to provide at least the resolution required by that number. For the equipment used in this work, there are 256 pixels in the x direction (shadowing direction) and 240 pixels in the y direction. The light intensity value for each pixel is digitized to 8 bits (the 8 bits being the binary representation of the light intensity), giving a range of values from 0 to 255.

A perfectly uniform sample does not lead to a detected image which is uniform in intensity. The slow variations which result are due to the illumination optics and the video camera response. The shading effects in the asperity images are corrected for each pixel according to the following formula:

$$I' = (I - D)/(W - D) \cdot IFAC,$$

where

I is the light intensity value for the pixel;

I' is the corrected light intensity value;

W is the light intensity value for the corresponding pixel in white reference;

D is the light intensity value for the corresponding pixel in dark reference; and IFAC is the scaling factor.

It has been found experimentally that a value of IFAC=200 is very satisfactory for the values of I, D, and W which are normally encountered when scanning a high quality transparent film (such as, for example, polyethylene terephthalate film used in video tapes). With this scaling factor, the value of I' always falls within the desired 0–255 range, provided the maximum light intensity of the white reference is adjusted to fall within the range of 210–240. This is at present done manually by the operator in response to information provided by the computer means.

The above equation is further constrained to assure that the numerator I–D never is negative. Such an occurrence, due to the statistical nature of the intensity sampling, would be rare, and this constraint has a negligible consequence on the final results.

Microscope magnification is selected so that the smallest shadow length, l, to be measured in the field of vision is magnified to the length of at least one pixel. There are various ways of accomplishing this objective, the simplest being by projecting on the display means screen the image of a standard reticle having parallel lines spaced at desired intervals as well as similarly parallel computer-created lines, and adjusting the magnification until both sets of lines coincide. Another way of calculating the desired magnification is to first ascertain the size corresponding to one pixel (divide the width of the video camera active target by 256), which in the case of the particular equipment employed is 49.6 μm. In order to enlarge a minimum l of e.g. 0.3 μm to the pixel size, a magnification of $49.6 \div 0.3 \approx 165$ is required. This technique requires a separate means for adjustment of the video camera active target to an accurately known value.

Figure 3:
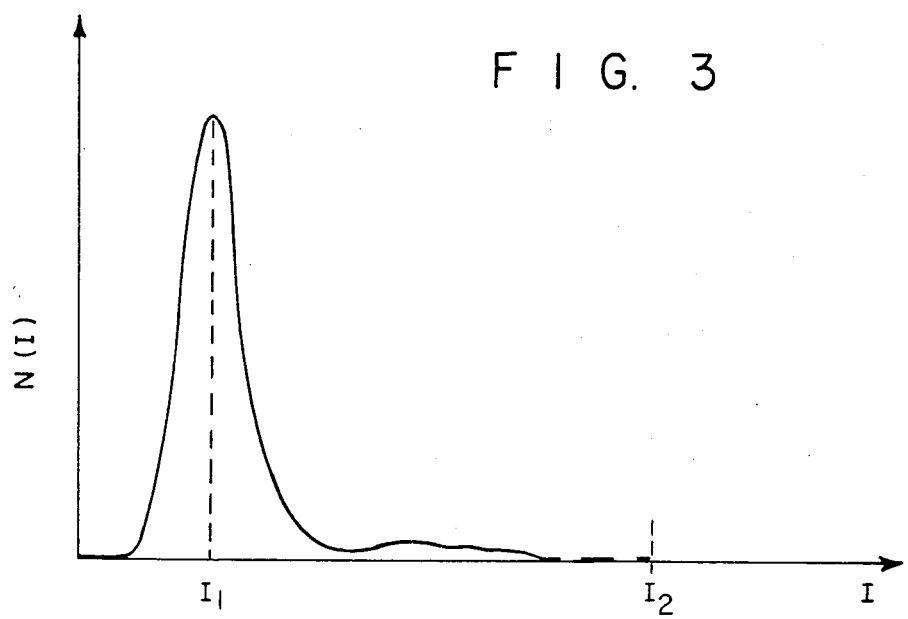
FIG. 3 is a plot of transmitted light intensity values vs. distribution of picture elements having a given light intensity.

A threshold value is calculated for each image, based on the distribution of the intensity values. FIG. 3 is an image intensity histogram, or a plot of light intensities versus intensity distribution, that is, number of picture elements for each intensity value. The large peak is due to background pixels, while the pixels corresponding to metallization shadows are represented by the small shoulder on the right hand side. The computer constructs the image histogram and finds the center, $I_1$, of the large peak by the least squares method based on a Gaussian model, using only part of the peak to the right of the center. It then finds the highest light intensity value (the brightest pixel), $I_2$, in the image and calculates the threshold intensity $I_T$, which corresponds to the intensity value at a predetermined fraction, F, of the distance between those two points.

$$I_T = I_1 + (I_2 - I_1) F.$$

It has been found experimentally that an F value of 0.4 gives consistent results, and this value is programmed into the computer operating memory. For lower F values, more of the background pixels would be detected, while for higher F values, fewer true asperity peaks would be detected. When so calculated, data obtained for different images (where $I_1$ and $I_2$ values may be different due to different light level settings and different amounts of background illumination) are consistent throughout the measurement.

Figure 4:
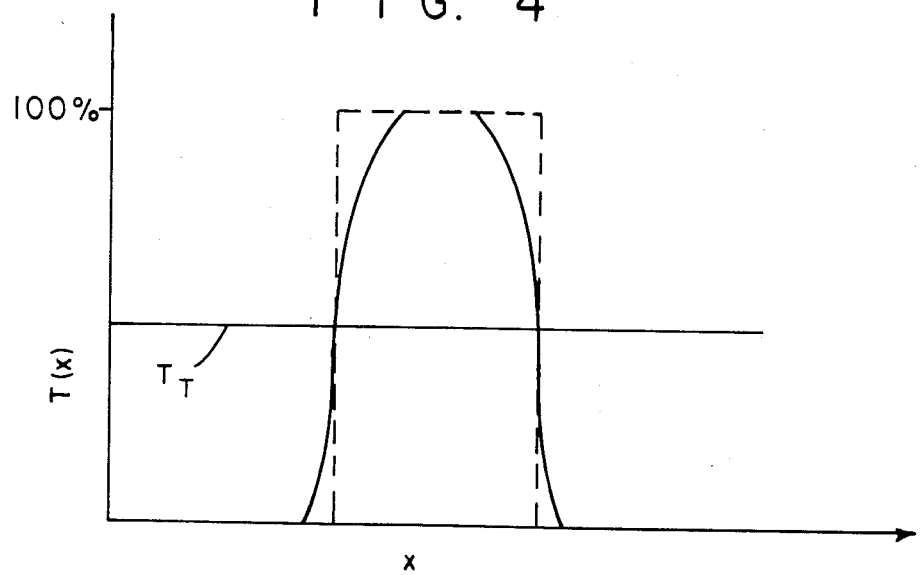
FIG. 4 is a plot of asperity distance through the longest length of the shadow vs. light transmission value at a given position, x.

FIG. 4 is a sample plot of intensity distribution for one asperity shadow, wherein x is the distance through the longest horizontal chord in the asperity shadow, and T(x) is the light transmission value (%) at position x. $T_T$ is the threshold transmission. In the ideal case of a well defined shadow with infinite contrast, any threshold larger than 0 would produce the same shadow size measurement, as shown by the broken lines. In the actual case, the shadow size measurement depends on the particular threshold selected. The computer processes the optical data to determine for each pixel whether its light transmission value T(x) lies above or below the threshold value $T_T$, and counts the number of pixels in which $T(x) > T_T$. By correlating that number with the length of one pixel, the computer calculates the length l of the asperity shadow (FIG. 2).

The actual calculation of the asperity height distribution is done by the microcomputer means, which processes the image which results from setting to zero the intensity of all pixels below the threshold value (cf. $T_T$, FIG. 4), to locate each asperity shadow and to measure shadow lengths. Although the length along the x direction is of interest, the processing is preferably done by going through the image one vertical (y) line at a time. The time required for processing a field is nearly independent of the number of asperity shadows present, and for the particular equipment used is about 20 seconds. The following rules have been set for the calculations:

Shadows which touch any of the image borders are not included in the analysis.

No assumptions are made about the shape of each shadow. The measured length is the longest length present in each shadow. This corresponds to the highest point on each asperity.

The analysis algorithm treats two shadows as distinct if no part of one shadow overlaps the smallest rectangle which encloses the other. In the case of such overlap, or in general for large, highly irregular shadows, the algorithm measures the longest length within the shadow, not counting the intervening spaces. Such rare cases have a negligible effect on the final asperity statistics.

The program provides visual feedback during the processing of a field, which can be followed on the display means (18, FIG. 5).

A typical printout of the calculation results is shown in FIG. 6. The printed information provides, among others, sample identification, date of manufacturing and date of testing, analysis identification, film area surveyed, number of asperities in the field, number of asperities per $mm^2$, mean and median asperity heights, standard deviation, actual asperity size distribution in steps of 0.1 $\mu m$, and an asperity height distribution histogram.

Equipment:

Metallizing equipment suitable for metallizing film samples according to this invention is available commercially. A Varian vacuum metallizer, available from Varian Associates (Palo Alto, Calif.), was found to be very satisfactory for this purpose.

An Olympus microscope, Model BHT, is used. It is equipped with 20×, 40×, and 60× objectives and 2.5× and 3.3× photo-eyepieces.

A Digital Equipment computer LSI-11/23 performs all the calculations. Data are stored on floppy discs such as Verbatim 5811, 3M 5411, BASF 5711 or equivalent.

Video digitizer is QFGO1 from Matrox Electronic Systems Ltd.

Image memory and digital-to-analog converter are two 4-bit dual function circuit boards, together providing 8-bit capacity, QRGD-256/4, from Matrox Electronic Systems Ltd.

Printer is LA120 Dec Writer, available from Ditigal Equipment Corporation.

The video camera is Dage-MTI, model SC-66.

The camera is modified, to assure response linearity over the entire range, by deactivating the auto-compensation circuitry.

The display means is Sanyo monitor, model VM 4512.

Asperity Height Distribution Determination

A commercial glass reticle having parallel lines etched on its surface at the desired intervals, for example 10 $\mu m$, is mounted on the microscope stage and illuminated with light source 11 (FIG. 5). The image of the line pattern is projected on the display means screen (18, FIG. 5). The microcomputer also creates a set of parallel lines on the screen, which usually will be at different intervals whose spacing is calculated as follows: Let us assume that it is desired that 0.3 $\mu m$ (equal to the resolution of the microscope, as explained above) be magnified to the size of one pixel; then the distance of 10 $\mu m$ will correspond to 33.3 pixels, and the computer creates lines, using integer approximation, which are 33.3 pixels apart. The height of the camera is then adjusted so that the reticle image is made to coincide with the calculated lines. This adjustment may require a small amount of refocusing of the microscope, which has a negligible effect on the image quality.

The reticle then is removed and a plain transparent slide (white reference) is placed on the microscope stage. If the test film has some opacity, e.g., due to the presence of fillers, a piece of unmetallized film is placed on the slide. The image then is scanned with the video camera, and the resulting videoscan is digitized and stored in the memory means. The light path then is redirected so that light does not reach the video camera. Again, a videoscan is made, digitized, and stored in the memory means as the dark reference. These two images are necessary for the calculation of the corrected light intensity, I', as explained above. With respect to equipment calibration in a similar type of operation see, for example, the article by P. A. Jansson et al. entitled "Implementation and application of a method to quantitate 2-D gel electrophoresis patterns", Electrophoresis, 1983, 4, 82–91.

Once these preliminary steps have been taken, a metallized film sample is mounted on a microscope slide and scanned with the video camera in a series of fields. The size of each field depends on the magnification, but with the equipment used and a magnification of 165, it is about 0.004 $mm^2$. For the purpose of routine examination, 25 fields are examined for each sample, the operator randomly changing each time the slide position on the microscope stage. The computer calculates then not only the asperity height distribution for each field but also the total distribution for all the 25 fields.

A typical computer printout gives, in addition to numerical information, also a graphic representation (or a computerized histogram) of the particle size distribution, as shown in FIG. 6.

The results obtained with the microscopical image analyzer of this invention are reproducible and are believed to be highly accurate. The system permits fast, routine analysis capable of use in a plant quality control laboratory. Although based on an old and well known principle, it puts that old principle to practical use. Prior methods employing the same principle were at most of limited interest, for non-routine inspection of transparent films, where time was not of the essence, and the accuracy of each determination depended to a large extent on the subjective examination of samples by a given individual.

It is readily apparent from the above discussion that the method of this invention can be applied to the detection and quantitative determination of any three-dimensional particles or imperfections on the film surface, not only those which are introduced on purpose but also those which are considered undesirable. In this manner, a microscopical image analyzer of the above-described type used in the above described manner becomes a quality control tool for routine film inspection.

We claim:

1. In a method of inspecting a transparent film having asperities distributed over its surface, that includes the steps of metallizing the film surface by vapor deposition of a metal impacting the film surface at a preselected shadowing angle to form transparent metallizing shadows adjacent each asperity, illuminating a metallized film sample, and examining an area of the film surface with an optical microscope placed in the path of the light illuminating the sample and transmitted through the metallizing shadows to determine the number and lengths of said metallizing shadows and therefrom the asperity height distribution, the improvement comprising:
   (a) scanning the field of view of the microscope with a video camera to detect metallizing shadows therein,
   (b) generating signals responsive to the transmitted light intensity for each metallizing shadow and comparing them with a calculated threshold value adapted to each image, and
   (c) from the signal amplitudes at least equal to the threshold values and from the preselected shadowing angle,, automatically calculating the asperity height distribution within the field of view.

2. The method of claim 1 wherein the videoscan produced by the video camera is digitized according to the number of pixels in the field of view, the microscope magnification being selected so that the smallest metallizing shadow length to be measured is magnified to the length of at least one pixel.

3. The method of claim 2 wherein the desired magnification is obtained by projecting the image of a standard reticle having parallel lines spaced at desired intervals, viewed through the microscope by the video camera, on the screen of a display means, computer-creating similarly parallel lines on the screen of the display means, and adjusting the microscope magnification until both sets of lines coincide.

4. The method of claim 1 wherein the transparent film is metallized by vapor deposition of aluminum.

5. The method of claim 4 wherein the film is a poly(ethylene terephthalate) film.

* * * * *